(12) United States Patent
Green et al.

(10) Patent No.: US 11,471,370 B2
(45) Date of Patent: Oct. 18, 2022

(54) INTIMATE ACCESSORY SYSTEM AND METHOD

(71) Applicants: Maya Green, Chicago, IL (US); Lindsay Lewis, Hollywood, FL (US)

(72) Inventors: Maya Green, Chicago, IL (US); Lindsay Lewis, Hollywood, FL (US)

( * ) Notice: Subject to any disclaimer, the term of this patent is extended or adjusted under 35 U.S.C. 154(b) by 598 days.

(21) Appl. No.: 16/580,889

(22) Filed: Sep. 24, 2019

(65) Prior Publication Data

US 2020/0016028 A1 Jan. 16, 2020

Related U.S. Application Data

(62) Division of application No. 15/423,125, filed on Feb. 2, 2017, now Pat. No. 10,420,700.

(60) Provisional application No. 62/291,417, filed on Feb. 4, 2016.

(51) Int. Cl.
| | |
|---|---|
| *A61H 19/00* | (2006.01) |
| *G06Q 30/06* | (2012.01) |
| *A61B 5/107* | (2006.01) |
| *A61H 21/00* | (2006.01) |
| *A61H 23/02* | (2006.01) |

(52) U.S. Cl.
CPC ........... *A61H 19/44* (2013.01); *A61B 5/1076* (2013.01); *A61H 21/00* (2013.01); *A61H 23/02* (2013.01); *G06Q 30/0621* (2013.01); *A61B 2503/12* (2013.01); *A61H 2201/0107* (2013.01); *A61H 2201/0153* (2013.01); *A61H 2201/1628* (2013.01); *A61H 2201/1652* (2013.01); *A61H 2201/1685* (2013.01); *A61H 2201/5038* (2013.01)

(58) Field of Classification Search
CPC ........ A61H 19/00; A61H 19/40; A61H 19/44; A61H 21/00; A61B 5/1076; G06Q 30/0621
See application file for complete search history.

(56) References Cited

U.S. PATENT DOCUMENTS

2020/0214617 A1* 7/2020 Sham .................... A61B 5/227

* cited by examiner

*Primary Examiner* — John P Lacyk
(74) *Attorney, Agent, or Firm* — The Concept Law Group, PA; Scott D. Smiley; Scott M. Garrett

(57) ABSTRACT

An interchangeable intimate accessory system including a first phallic device having a distal end and a proximal end, the distal end of the first phallic device being shaped for sexual application to a human orifice and the proximal end of the first phallic device being formed as a first connector; a second phallic device having a distal end and a proximal end, the distal end of the second phallic device being shaped and configured for sexual application to a human orifice and the proximal end of the second phallic device being formed as a second connector. The first and second phallic devices are removably couplable to one another, via the first and second connectors, to provide a dual-ended configuration when coupled together and an individual-use configuration when not coupled together.

9 Claims, 18 Drawing Sheets

INTIMATE ACCESSORY SYSTEM AND METHOD

CROSS-REFERENCE TO RELATED APPLICATION

This application is a divisional of, and claims priority to U.S. patent application Ser. No. 15/423,125, filed Feb. 2, 2017, and now U.S. Pat. No. 10,420,700, and to U.S. Provisional Patent Application No. 62/291,417 filed Feb. 4, 2016, the entirety of each of which are hereby incorporated by reference.

FIELD OF THE INVENTION

The present invention relates generally to intimate accessories, and, more particularly, relates to a system and/or method for providing customizable and interchangeable male reproductive organ substitutes.

BACKGROUND OF THE INVENTION

Intimate accessories such as phallic devices are well-known and have been used as male reproductive organ substitutes for many years. Such devices are primarily used for sexual pleasure for couple use, as well as, individual use. Known phallic devices are provided in predetermined shapes, sizes, and configurations. In other words, users are required to purchase phallic devices as is, without being able to pre-select features personalized for the user's particular desires and personal preferences. In addition, known phallic devices are limited and rather static in their structure and therefore use. Existing phallic devices are not made to be interchangeable and comfortably adaptable for individual use, as well as, couple use.

Therefore, a need exists to overcome the problems with the prior art as discussed above.

SUMMARY OF THE INVENTION

The invention provides an intimate accessory system and method that overcomes the hereinafore-mentioned disadvantages of the heretofore-known devices and methods of this general type and that may be personalized and interchangeable.

With the foregoing and other objects in view, there is provided, in accordance with the invention, an interchangeable intimate accessory system including a first phallic device having a distal end and a proximal end, the distal end of the first phallic device being shaped and configured for sexual application to a human orifice and the proximal end of the first phallic device being formed as a first connector; and a second phallic device having a distal end and a proximal end, the distal end of the second phallic device being shaped and configured for sexual application to a human orifice and the proximal end of the second phallic device being formed as a second connector, the first phallic device and the second phallic device being removeably couplable to one another, via coupling of the first and second connectors, so as to provide a dual-ended configuration when coupled together and an individual-use configuration when not coupled together.

In accordance with another feature of the present invention, the dual-ended configuration has the distal end of the first phallic device and the distal end of the second phallic device disposed at opposite ends when the first phallic device and the second phallic device are coupled together via the first connector and the second connector.

In accordance with another feature, an embodiment of the present invention includes an intermediate universal connector with a first end and a second end, the first end of the intermediate universal connector matingly couplable to the first connector of the first phallic device and the second end of the intermediate universal connector matingly couplable to the second connector of the second phallic device so as to selectively provide the dual-ended configuration when the intermediate universal connector is matingly coupled to and disposed between the first and second phallic devices.

In accordance with another feature of the present invention, each of the first end and the second end of the intermediate universal connector includes a plurality of prongs and each of the first connector of the first phallic device and the second connector of the second phallic device is formed with a plurality of mating prong-receptacles.

In accordance with yet another feature, an embodiment of the present invention includes an end cover base portion disposed to removeably couple to and cover at least one of the first connector at the proximal end of the first phallic device and the second connector at the proximal end of the second phallic device so as to selectively provide at least a portion of a gripping surface for the individual-use configuration when the intermediate universal connector is not coupled to the at least one of the first connector and the second connector.

In accordance with a further feature of the present invention, each of the first connector of the first phallic device and the second connector of the second phallic device is formed as one of a female connector and a male connector; and each of the first end and the second end of the intermediate universal connector is formed as a mating connector to the one of the female connector and the male connector.

In accordance with another feature of the present invention, the intermediate universal connector is formed as an angular-shaped body with a first arm portion having the first end of the intermediate universal connector and a second arm portion having the second end of the intermediate universal connector, the first and second arm portions disposed relative to one another such that when the first phallic device is matingly coupled to the first end and the second phallic device is matingly coupled to the second end the distal end of the first phallic device and the distal end of the second phallic device are oriented at between 45 degrees to 135 degrees relative to one another.

In accordance with another feature, an embodiment of the present invention includes at least a third phallic device having a distal end and a proximal end, the distal end of the third phallic device being shaped and configured for sexual application to a human orifice and the proximal end of the third phallic device being formed as a third connector, the third connector matingly couplable to at least one of the first and second ends of the intermediate universal connector so as to be interchangeable with the first and second phallic devices for selectively forming the dual-ended configuration.

In accordance with yet another feature, an embodiment of the present invention further includes a harness with an o-ring disposed thereon, the harness being operably configured to be worn on a portion of a human body and the o-ring disposed to be selectively couplable with one of the first connector and the second connector so as to secure the respective phallic device to the harness.

In accordance with a further feature of the present invention, each of the first and second phallic devices includes at least one vibrating element disposed to independently vibrate each of the first and second phallic devices in at least the dual-ended configuration.

In accordance with another feature, an embodiment of the present invention further includes at least one server operably configured to provide an Internet website for custom-ordering phallic devices and to cause at least one processor to display a first display portion of the Internet website, at a user computer terminal, including a plurality of user selection options for at least one custom-order phallic device with at least two user selection options for a phallic depth measurement and at least two user selection options for a phallic girth measurement, the plurality of user selection options for the at least one custom-order phallic device are configured to be selected by a user through the first display portion of the Internet website; and a phallic measurement kit including: at least one phallic depth measurement tool providing at least a dual-sensory indication of a plurality of user-selectable phallic depth measurements corresponding to the at least two user selection options for the phallic depth measurement provided via the first display portion of the Internet website; and at least one phallic girth measurement tool providing at least a dual-sensory indication of a plurality of user-selectable phallic girth measurements corresponding to the at least two user selection options for the phallic girth measurement provided via the first display portion of the Internet website. In accordance with a further feature of the present invention, at least one of the first phallic device and the second phallic device is ordered via the Internet website to be made according to one of the plurality of user-selectable phallic depth measurements and one of the plurality of user-selectable phallic girth measurements identified via the phallic measurement kit and selected, at the user computer terminal, via the first display portion of the Internet website.

In accordance with another feature, an embodiment of the present invention includes a system with at least one server operably configured to provide an Internet website for custom-ordering phallic devices and to cause at least one processor to: display a first display portion of the Internet website, at a user computer terminal, including a plurality of user selection options for at least one custom-order phallic device with at least two user selection options for a phallic depth measurement and at least two user selection options for a phallic girth measurement, the plurality of user selection options for the at least one custom-order phallic device are configured to be selected by a user through the first display portion of the Internet website; and a phallic measurement kit including: at least one phallic depth measurement tool providing at least a dual-sensory indication of a plurality of user-selectable phallic depth measurements corresponding to the at least two user selection options for the phallic depth measurement provided via the first display portion of the Internet website; and at least one phallic girth measurement tool providing at least a dual-sensory indication of a plurality of user-selectable phallic girth measurements corresponding to the at least two user selection options for the phallic girth measurement provided via the first display portion of the Internet website.

In accordance with another feature of the present invention, the server is further operably configured to cause the processor to receive, from the user computer terminal, via a second display portion of the Internet website, a request to make the at least one custom-order phallic device according to at least the user selections, input via the Internet website, of the plurality of user selection options for the phallic depth measurement and the phallic girth measurement.

In accordance with yet another feature of the present invention, the dual-sensory indication provided by the at least one phallic depth measurement tool includes a visual indication identifying each of the plurality of user-selectable phallic depth measurements and a tactile indication for an interior surface of the user's orifice corresponding to each of the plurality of user-selectable phallic depth measurements; and the dual-sensory indication provided by the at least one phallic girth measurement tool includes a visual indication identifying each of the plurality of user-selectable phallic girth measurements and a tactile indication for an interior surface of the user's orifice corresponding to each of the plurality of user-selectable phallic girth measurements.

In accordance with a further feature of the present invention, the tactile indication for the phallic depth measurement tool is formed as an elongated tubular body disposed for insertion within the user's orifice and the visual indication for the phallic depth measurement tool includes a plurality of gradient markings visible on and extending along a length of the elongated tubular body.

In accordance with yet a further feature of the present invention, the visual indication and the tactile indication for the phallic girth measurement tool includes a plurality of tubular bodies each having a different visually identifiable diameter and disposed for insertion within and tactile contact with an interior surface of the user's orifice.

In accordance with yet another feature of the present invention, the phallic depth measurement tool is formed as a universal hollow tubular vagina inserter with a plurality of gradient markings each visually indicating the plurality of user-selectable phallic depth measurements provided via the Internet website and the universal hollow tubular vagina inserter disposed for insertion within the user's orifice for a tactile indication of a desired one of the plurality of user-selectable phallic depth measurements; and the phallic girth measurement tool including a plurality of tubular bodies disposed for vaginal insertion, each tubular body having a diameter that is different than a diameter of each of the other tubular bodies and each diameter corresponding to one of the plurality of user-selectable phallic girth measurements provided via the Internet website.

In accordance with yet another feature of the present invention, the at least one custom-order phallic device includes a first phallic device having a distal end and a proximal end, the distal end of the first phallic device being shaped and configured for sexual application to a human orifice and the proximal end of the first phallic device being formed as a first connector; a second phallic device having a distal end and a proximal end, the distal end of the second phallic device being shaped and configured for sexual application to a human orifice and the proximal end of the second phallic device being formed as a second connector, the first phallic device and the second phallic device being removeably couplable to one another, via coupling of the first and second connectors, so as to provide a dual-ended configuration when coupled together and an individual-use configuration when not coupled together; and at least one of the first phallic device and the second phallic device is ordered via the Internet website to be made according to one of the plurality of user-selectable phallic depth measurements and one of the plurality of user-selectable phallic girth measurements identified via the phallic measurement kit and selected, at the user computer terminal, via the Internet website.

In accordance with another feature of the present invention, the plurality of user selection options for the at least one custom-order phallic device included in the first display portion of the Internet website further includes: a color option; a vibration option; and a plurality of phallic device shape options.

In accordance with the present invention, a method for making at least one personalized phallic device is disclosed, the method including a step of mailing, to a user, an enclosed package including a phallic measurement kit with: at least one phallic depth measurement tool providing at least a dual-sensory indication of a plurality of user-selectable phallic depth measurements corresponding to at least two user selection options for the user-selectable phallic depth measurements provided via a first display portion of an Internet website; and at least one phallic girth measurement tool providing at least a dual-sensory indication of a plurality of user-selectable phallic girth measurements corresponding to at least two user selection options for the user-selectable phallic girth measurements provided via the first display portion of the Internet website. In a further embodiment of the present invention, the method may further includes steps of after mailing to the user, displaying, by at least one server, the first display portion of the Internet website, at a computer terminal associated with the user, the first display portion displaying a plurality of user selection options for at least one custom-order phallic device including the at least two user selection options for the user-selectable phallic depth measurement and the at least two user selection options for the user-selectable phallic girth measurements, the plurality of user selection options for the at least one custom-order phallic device are configured to be selected by the user through the first display portion of the Internet website; receiving, by the server, from the computer terminal associated with the user, a request to make the at least one custom-order phallic device according to at least the user selections, input via the Internet website, corresponding to the plurality of user selection options for the phallic depth measurement and the phallic girth measurement; and as a result of receiving the request, causing the custom-order phallic device to be made by one of three-dimensional printing and manufacturing with a three-dimensional mold according to at least the user selections, input via the Internet website, corresponding to the plurality of user selection options for the phallic depth measurement and the phallic girth measurement.

Although the invention is illustrated and described herein as embodied in an intimate accessory system and method, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the phallic device from a first end to a second opposing end. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
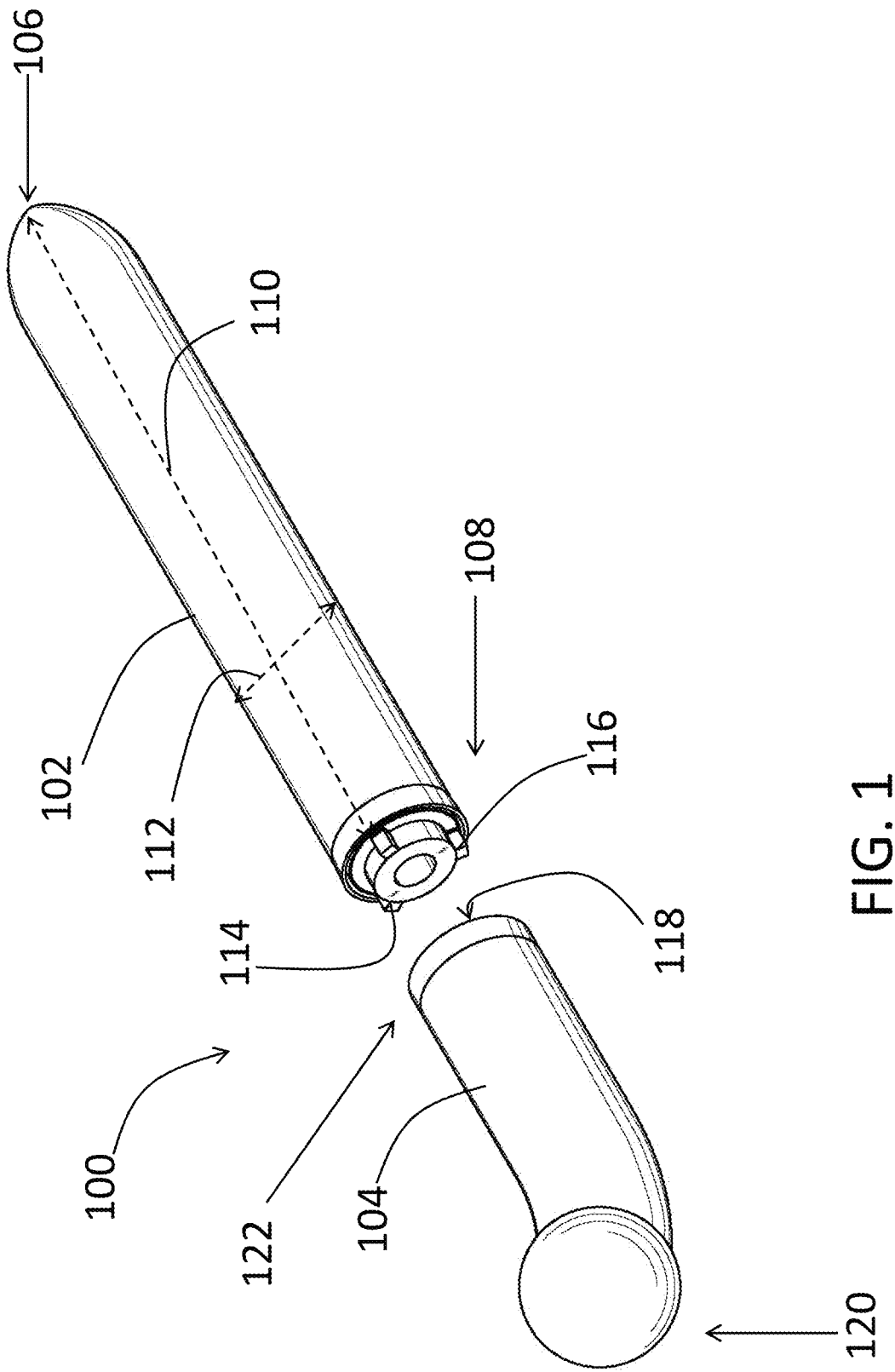
FIG. 1 is a perspective view of a first exemplary interchangeable intimate accessory system with a first phallic device and a second phallic device, shown unconnected to one another, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient interchangeable intimate accessory system. Embodiments of the invention provide for a system with at least a first phallic device and a second phallic device removeably couplable with one another for selective dual or individual use. In addition, embodiments of the invention provide for an intermediate universal connector between first and second phallic devices for removeably coupling the phallic devices to one another. Additional embodiments of the present invention provide for an end cover base portion that removeably fits over a connector end of the phallic device to cover the connector end and also provide a gripping surface for individual use of the phallic device, when not being used in a dual configuration. Furthermore, some embodiments of the present invention provide for a novel and inventive phallic measurement kit that provides users with at least a dual-sensory indication of selectable girth and depth measurement options for a phallic device. Yet further embodiments of the present invention include a website configured to receive measurement options indicated in the measurement kit for ordering and personalizing the phallic devices according to the users' personal desires and preferences.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. The first example of an interchangeable intimate accessory system 100, as shown in FIG. 1, includes a first phallic device 102 and a second phallic device 104 each configured to be removeably couplable with one another for selective use in a dual-ended configuration (primarily for couple use) and an individual-use configuration, as will be discussed in more detail below.

The first phallic device 102 may have an elongated shape, as with many known phallic devices. In one embodiment, a depth 110 of the first phallic device 102 may be any known depth of such devices, such as, for example, 3 to 13 inches. In other embodiments, the depth 110 may be outside of this range. In one embodiment, a girth 112 of the first phallic device 102 may be any known girth of such devices, such as, for example, 2.5 to 4.5 inches. In other embodiments, the girth 112 may be outside of this range. In another embodiment, the first phallic device 102 may be other shapes, such as, circular. In yet another embodiment, the first phallic device 102 may be considered cylindrical in shape with a convex shaped end. In other embodiments, the first phallic device 102 may be formed as other shapes and sizes.

The first phallic device 102 may be made of a silicone material. In another embodiment, the first phallic device 102 may be made of another polymer-based material, or any other known material that phallic devices are generally constructed of. In one embodiment, the first phallic device 102 may be made of a pliable material. In other embodiments, the first phallic device 102 may be made of a substantially firm material. In yet other embodiments, the first phallic device 102 may be provided with a rigid core, yet be surrounded by a more flexible, resilient material on its exterior surface.

In one embodiment, the first phallic device 102 may have a smooth texture, or exterior surface. In other embodiments, the first phallic device 102 may have a rough, texturized exterior surface. In one embodiment, the first phallic device 102 may have a generally linear shape. In other embodiments, the first phallic device 102 may be curve-shaped. In yet other embodiments, the first phallic device 102 may have additional arms or protrusions extending therefrom. For example, the first phallic device 102 may have additional arms or protrusions extending from the main body for clitoral stimulation, for example, or other non-penetration stimulation. The first phallic device 102 may be provided with an exterior surface of any known color.

In one embodiment, the first phallic device 102 may be vibrating. In another embodiment, the first phallic device 102 may be non-vibrating. In yet another embodiment, the first phallic device 102 may include at least one vibrating element 200 (FIG. 2) disposed to vibrate independently of the second phallic device 104 in the single-use configuration, as well as, the dual-ended configuration. In yet a further embodiment, the second phallic device 104 also has a vibrating element 202 (FIG. 2) that is disposed to vibrate independently of the first phallic device 102 in the same manner. Advantageously, independent vibration can be provided for added versatility and personalization of use, even in the dual-ended configuration. The vibrating element 202 may be a motor electrically coupled to an actuator, such as a button or a switch, disposed on the outside of each respective phallic device.

In yet other embodiments, the first phallic device 102 may be made of other materials and with various other properties and features that known phallic devices are generally constructed of. Further, the second phallic device 104 may be provided in various shapes and sizes, and with various materials, surface feels, colors, and other features as described above with reference to the first phallic device 102. Therefore, the description above with reference to the first phallic device 102 will not be expressly repeated herein for the second phallic device 104, but does apply to the second phallic device 104.

Importantly, embodiments of the present invention allow users to personalize the phallic devices and/or the system 100 according to their personal desires and preferences, rather than selecting from a multitude of predetermined/premade phallic devices, as will be described herein in more detail below, with reference to the flow chart of FIG. 12.

In preferred embodiments of the present invention, the phallic devices 102, 104 are configured to be selectively couplable with one another forming the system 100. The first phallic device 102 may be considered to have a distal end 106 and a proximal end 108. The distal end 106 may be disposed opposite the proximal end 108. The distal end 106 may be shaped and configured for sexual application as a male reproductive organ substitute. More specifically, in one embodiment, the distal end 106 is sized, shaped, and configured for sexual application, or penetration into a human orifice (e.g., vagina). In one embodiment, the distal end 106 may be a rounded end. In another embodiment, the distal end 106 may be a semi-circle or slightly pointed end.

The second phallic device 104 may also be considered to have a distal end 120 and a proximal end 122. The distal end 120 may be disposed opposite the proximal end 122. The distal end 120 may be shaped and configured for sexual application as a male reproductive organ substitute. More specifically, in one embodiment, the distal end 120 is sized, shaped, and configured for sexual application, or penetration into a human orifice (e.g., vagina). In one embodiment, the distal end 120 may be a rounded end. In another embodiment, the distal end 120 may be a semi-circle or slightly pointed end. Many shapes for various male reproductive organ substitutes are known and may be provided with embodiments of the present invention.

Figure 3:
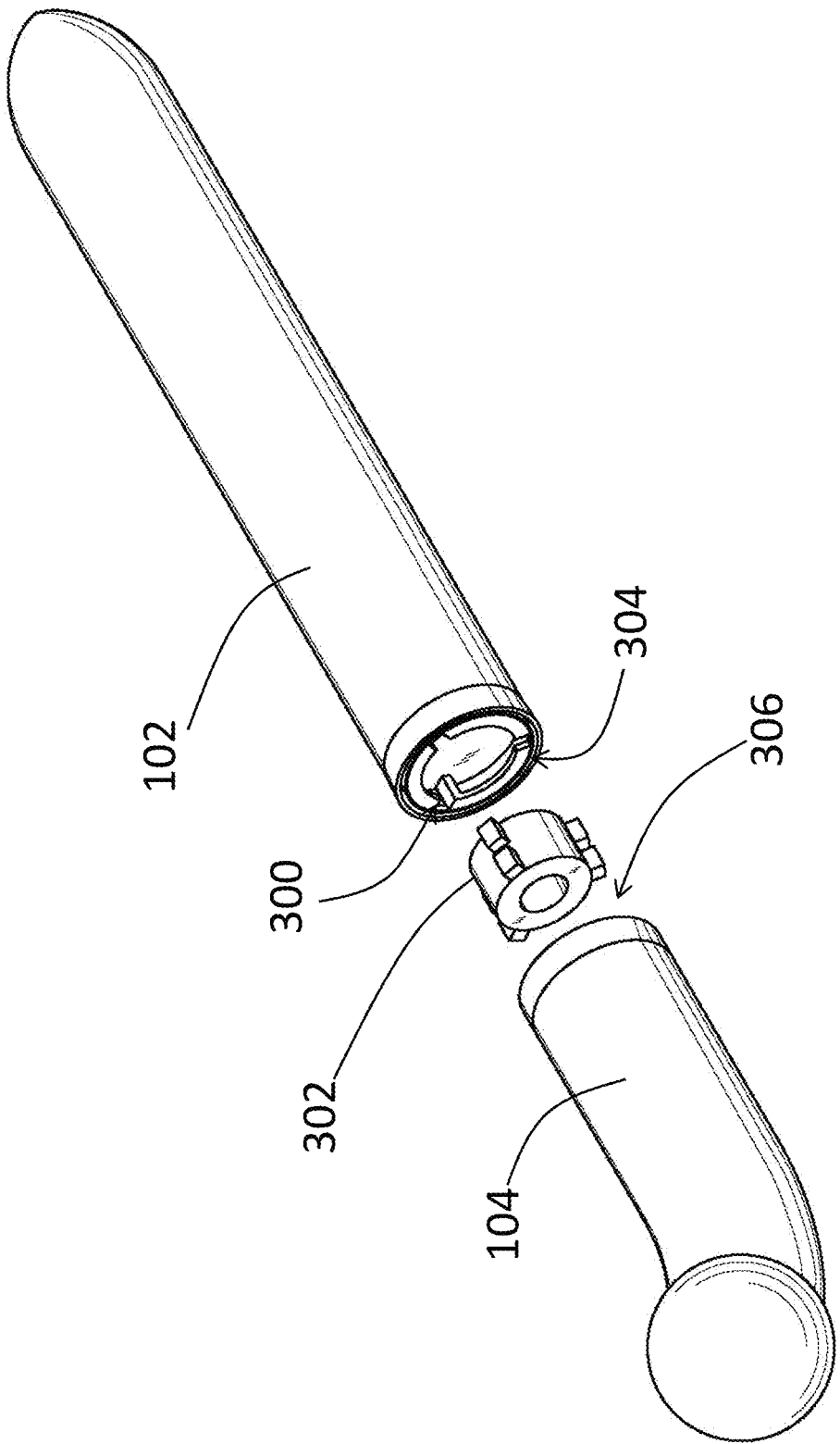
FIG. 3 is a perspective view of a second exemplary interchangeable intimate accessory system with a first phallic device, a second phallic device, and an intermediate universal connector, shown unconnected to one another, in accordance with the present invention.

The proximal end 108 of the first phallic device 102 may be formed as a first connector 114. In one embodiment, the first connector 114 may be formed as a male connector 114, such as, by including one or more protrusions. In a further embodiment, the first connector 114 may include a plurality of prongs 116 sized and shaped to mate with a plurality of mating prong-receptacles 300 (FIG. 3) corresponding to a female connector 118 disposed on the proximal end 122 of the second phallic device 104. In an embodiment where the first phallic device 102 is directly couplable to the second phallic device 104, as in FIG. 1, the mating female connector 118 is disposed on the second phallic device 104. Of course, the mating connectors may be switched in some embodiments, with the male connector 114 provided on the second phallic device 104 and the female connector 118 provided on the first phallic device 104. The male and female connectors disposed on the proximal ends 108, 122 of the phallic devices 102, 104 allow the devices to be securely matingly coupled together to form the dual-ended configuration of the system 100.

Figure 2:
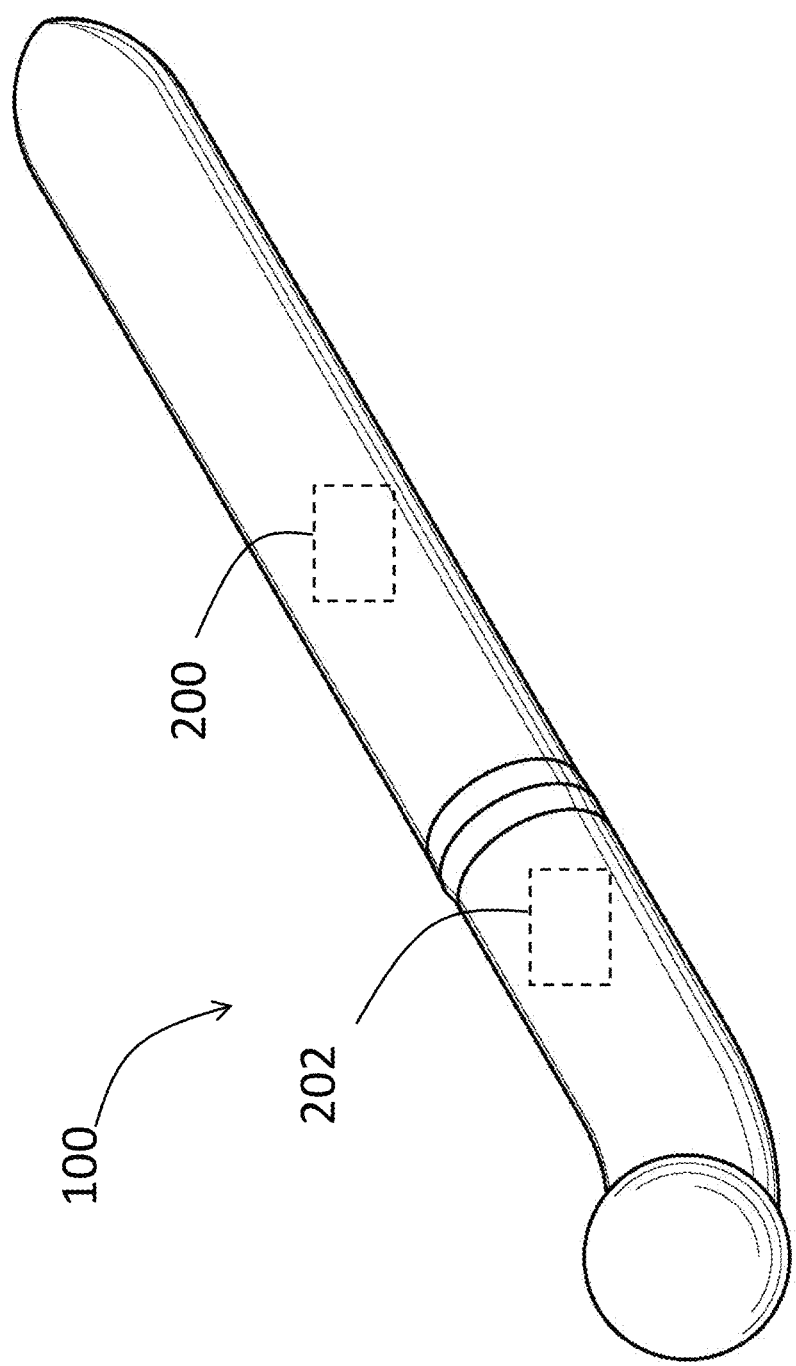
FIG. 2 is a perspective view of the interchangeable intimate accessory system of FIG. 1, with the first and second phallic devices shown connected together, in accordance with the present invention.

In one embodiment, the mating connectors 114, 118 may be configured to couple together by insertion of the male prongs 116 into the corresponding prong-receptacles 300 (FIG. 3) and by a subsequent twisting motion to lock the male prongs 116 into the female connector 118. Accordingly, the first and second phallic devices 102 and 104 are removeably couplable to one another, via coupling the female and male connectors 118, 114, so as to provide the dual-ended configuration (when coupled together, as in FIG. 2) and an individual-use configuration (when not coupled together, as in FIG. 1). Stated another way, the dual-ended configuration may be provided such that the distal ends 106, 120 are disposed at opposite ends of the system 100 when the first phallic device 102 and the second phallic device 104 are coupled together via the connectors 118, 114, the connectors 118, 114 being disposed on the proximal ends 122, 108 where the connection takes place. As can be seen in FIG. 2, the proximal ends 122, 108 and the connectors 118, 114 should be configured such that when the devices 102, 104 are connected together the system 100 appears to be a uniform dual-ended device. In other words, the connectors 118, 114 should not be visible when the devices 102, 104 are connected and the area where the two devices 102, 104 meet should provide a uniform and aesthetically pleasing surface and preferably is configured as a gripping surface for ease of use.

Referring now primarily to FIGS. 3-6, in one embodiment, the interchangeable intimate accessory system 100 may include an intermediate universal connector 302, rather than being configured for direct connection, as in the embodiment depicted in FIGS. 1-2.

The intermediate universal connector 302 is configured such that both the first and second phallic devices 102 and 104 are couplable to the intermediate universal connector 302 to form the dual-ended configuration. In one embodiment, the intermediate universal connector 302 is configured as an intermediate universal male connector 302 and each of the phallic devices 102, 104 configured for use in the system 100 has a mating female connector 304, 306, respectively. Such embodiments with the intermediate universal connector 302 are advantageous (over embodiments with direct coupling such as depicted in FIGS. 1-2) in that all the interchangeable phallic devices 102, 104 configured for use in the system 100 may be formed with the same type of connector. This provides uniformity and reduces complexity of use and manufacturing costs. In particular, embodiments of the present invention may provide for an end cover base portion 700 that covers the connector for the individual-use configuration. With all the phallic devices 102, 104 having the same connector type, the end cover base portions 700 may also be manufactured with the same mating connector type. It should be understood that although the exemplary embodiment depicts the intermediate universal connector 302 as a male connector, alternative embodiments may also be provided such that the intermediate universal connector 302 is a female connector, and the phallic devices 102, 104 may then be configured with mating male connector parts.

Figure 4:
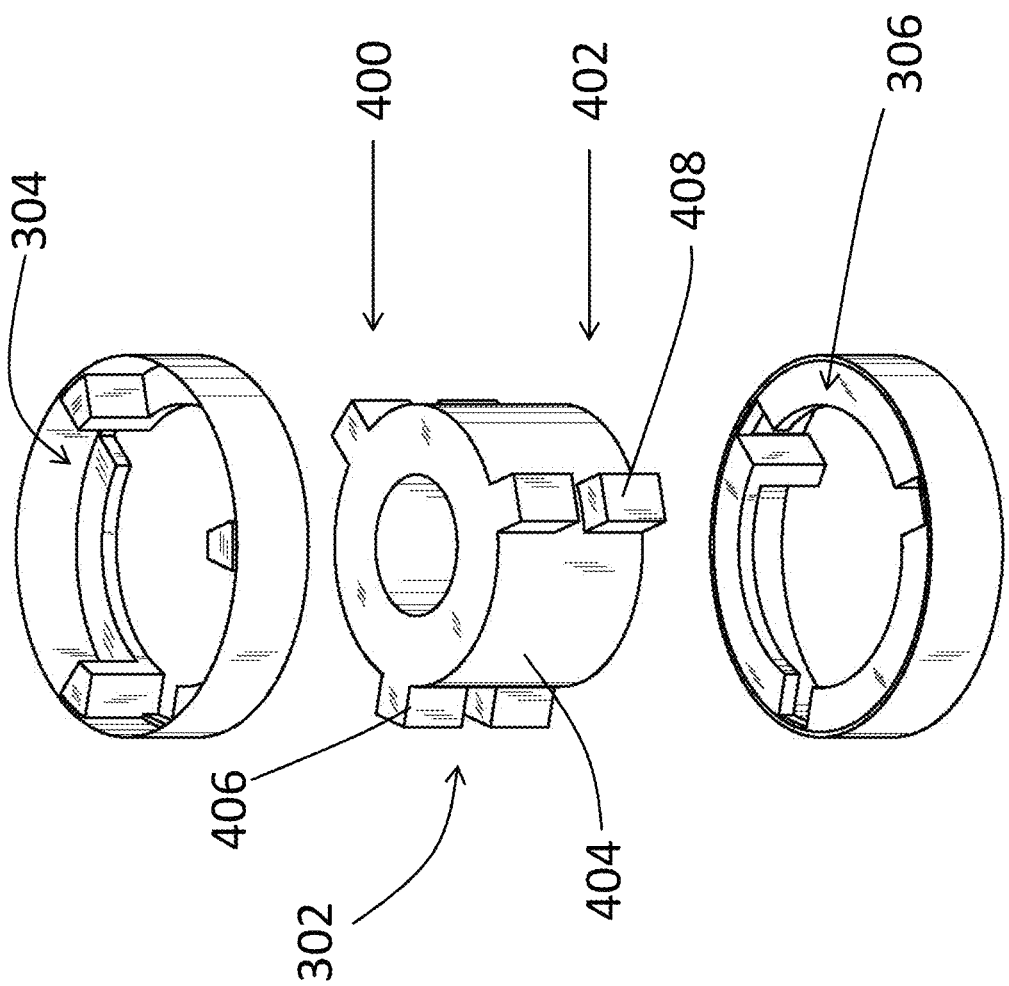
FIG. 4 is a partial, exploded, downward-looking perspective view of the intermediate universal connector and the mating connector portions of the first and second phallic devices of FIG. 3, in accordance with the present invention.
Figure 5:
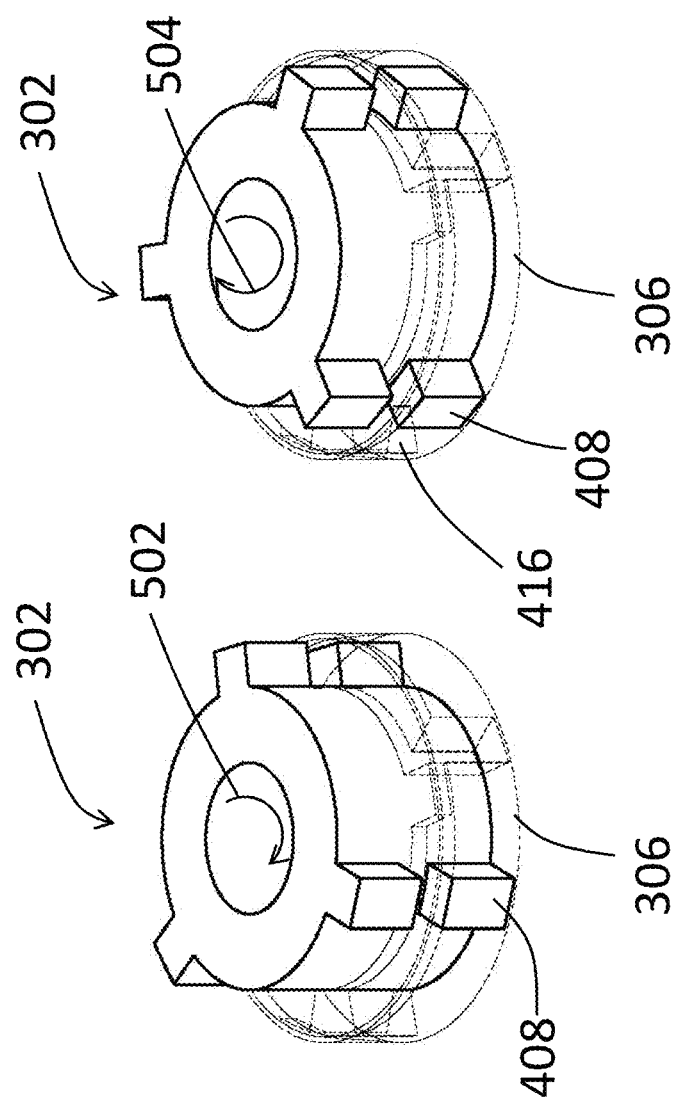
FIG. 5 is a partial, partially cross-sectional, downward-looking perspective view of the intermediate universal connector and the mating connector portions of the first and second phallic devices of FIG. 3, shown being connected together, in accordance with an exemplary embodiment of the present invention.
Figure 6:
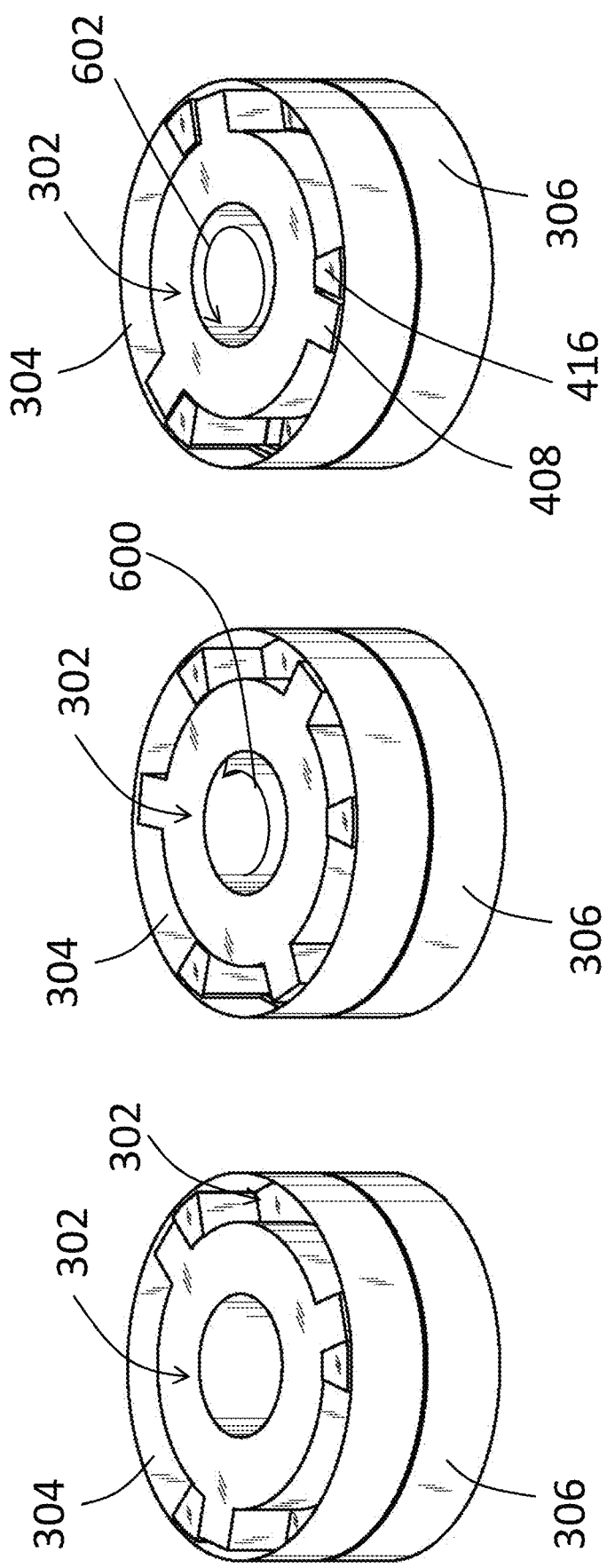
FIG. 6 is a partial downward-looking perspective view of the intermediate universal connector and the mating connector portions of the first and second phallic devices of FIG. 3, shown being connected together, in accordance with the present invention.

In one embodiment, the intermediate universal connector 302 includes a first end 400 and a second end 402. In a further embodiment, the first end 400 is disposed opposite the second end 402. In one embodiment, the intermediate universal connector 302 can be considered to have a main body 404 with a plurality of prongs 406 extending outwardly and disposed on the first end 400 and a plurality of prongs 408 extending outwardly and disposed on the second end 402. Each of the plurality of prongs 406, 408 is operably configured to matingly engage the connectors 304, 306 on the phallic devices 102, 104, respectively. FIGS. 4-6 provide partial views of the connectors, shown without the actual body of the phallic devices, for clarity. As shown in FIGS. 5-6, the connector 306 on the phallic device 104 may be connected to the intermediate universal connector 302. Specifically, the prongs 408 of the intermediate universal connector 302 may be inserted into the corresponding mating prong-receptacles 500 on the respective connector 306 and subsequently rotated in one of a clockwise or counter-clockwise direction (depending on the particular configuration), as indicated by the arrows 502, 504, until the prongs 408 abut a barrier 416 or tab on the connector 306 that locks the connection in place; that is, until the users rotates the prongs 408 in the opposite direction, as indicated by the arrows 600, 602, in order to uncouple the connectors 306, 304 from the intermediate universal connector 302).

In one embodiment, the main body 404 of the intermediate universal connector 302 may be annular-shaped. In another embodiment, the main body 404 may be provided in other shapes. In one embodiment, each end 400, 402 of the intermediate universal connector 302 may have three prongs 406, 408. In another embodiment, each end 400, 402 of the intermediate universal connector 302 may have more or less than three prongs 406, 408, but should still be configured to be removeably couplable to the connectors 304, 306 so as to selectively provide the dual-ended configuration in a secure manner when the intermediate universal connector 302 is coupled to and disposed between the first and second phallic devices 102, 104.

Figure 7:
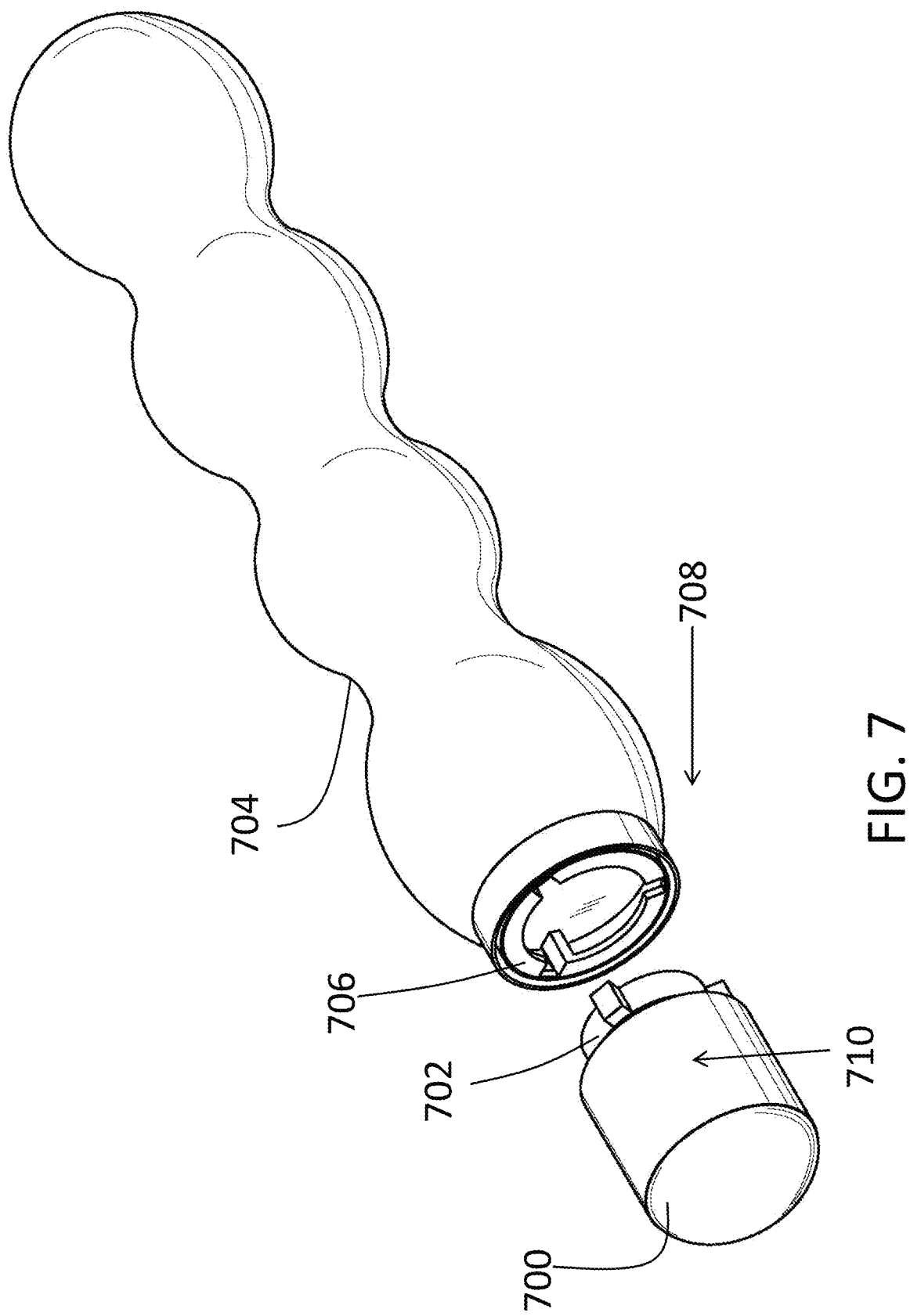
FIG. 7 is a perspective view of a third phallic device, interchangeable with one of the other phallic devices of the system of FIG. 3, and an end cover portion removeably couplable to any one of the first, second, or third phallic devices for selective individual use thereof, in accordance with an embodiment of the present invention.

Referring now primarily to FIG. 7, the end cover base portion 700 is illustrated in an exemplary embodiment for the single-use configuration of the phallic device. Stated another way, it is desirable to provide a gripping surface for the single-use configuration of the phallic device, and/or visually and physically conceal the connecting portion of the phallic device. Accordingly, the end cover base portion 700 may be provided with an end cover connector 702.

In FIG. 7, yet a third phallic device 704 is illustrated, showing a textured surface. It should be understood that the third phallic device 704 is selectively interchangeable with the first and second phallic devices 102, 104 in the system 100. The third phallic device 704 is provided with a mating connector 706 at a proximal end 708 thereof. Like the second phallic device 104, the third phallic device 704 may be provided in various shapes and sizes, and with various materials, surface feels, colors, and other features as described above with reference to the first phallic device 102. Therefore, the description above with reference to the first phallic device 102 will not be expressly repeated herein for the third phallic device 704, but does apply to the third phallic device 704.

Figure 8:
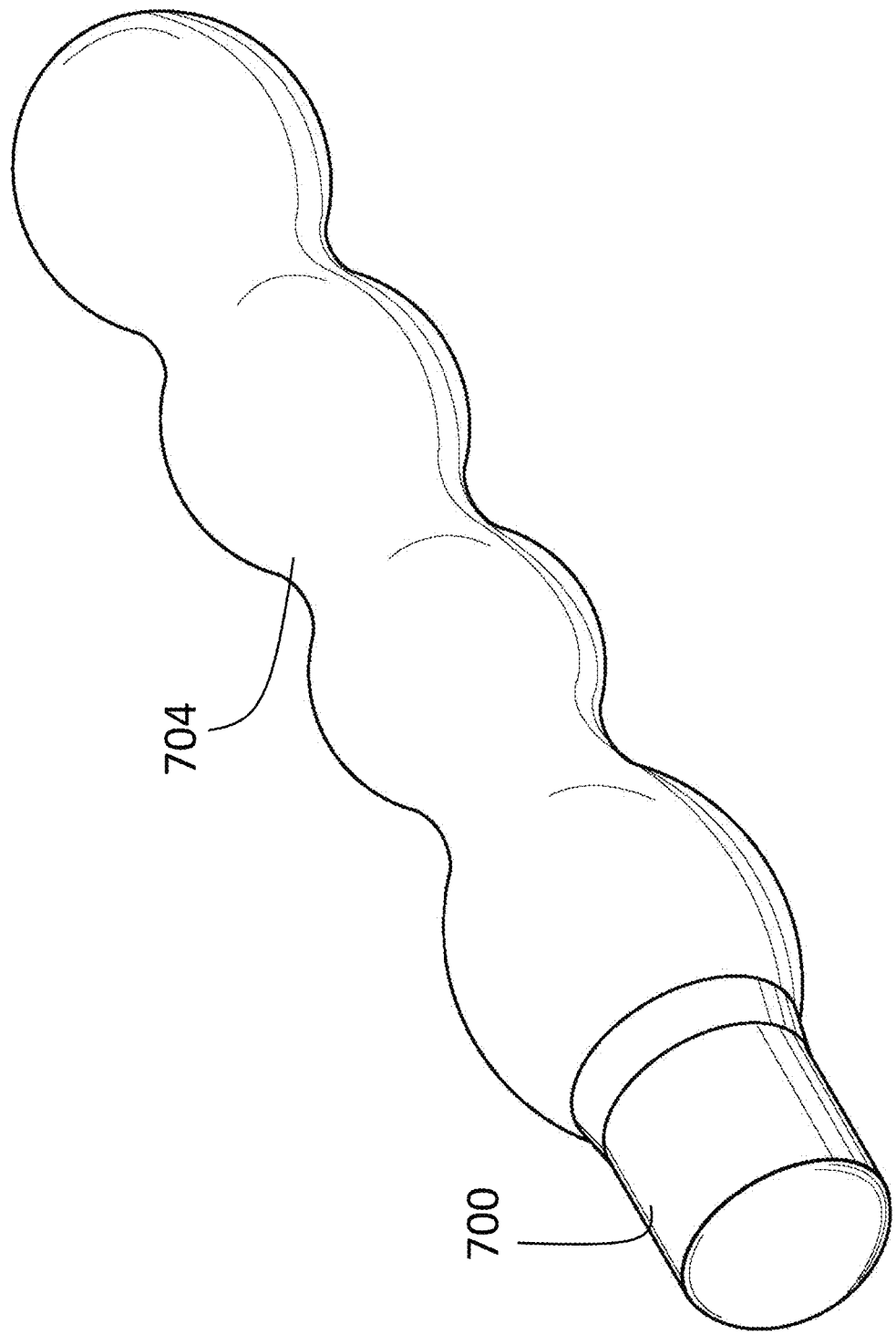
FIG. 8 is a perspective view of the third phallic device of FIG. 7 coupled to the end cover portion, in accordance with the present invention.

The end cover base portion 700 is configured to be removeably couplable to and cover the connector 706 on the proximal end 708 of the phallic device 704. The end cover base portion 700 is also operable to removeably couple to and cover the connectors 304, 306 on the first and second phallic devices 102, 104, respectively. Accordingly, a user need only purchase a single end cover base portion 700 that is operable to cover the open end of any phallic device that is configured for use with the system 100, when desired for the individual-use configuration. Advantageously, the end cover base portion 700 may also include a gripping surface 710 or handle portion, that allows the user to conveniently grip the phallic device 704 (or 102 or 104) when in the individual-use configuration, as shown in FIG. 8, being uncoupled from any mating phallic device.

Figure 9:
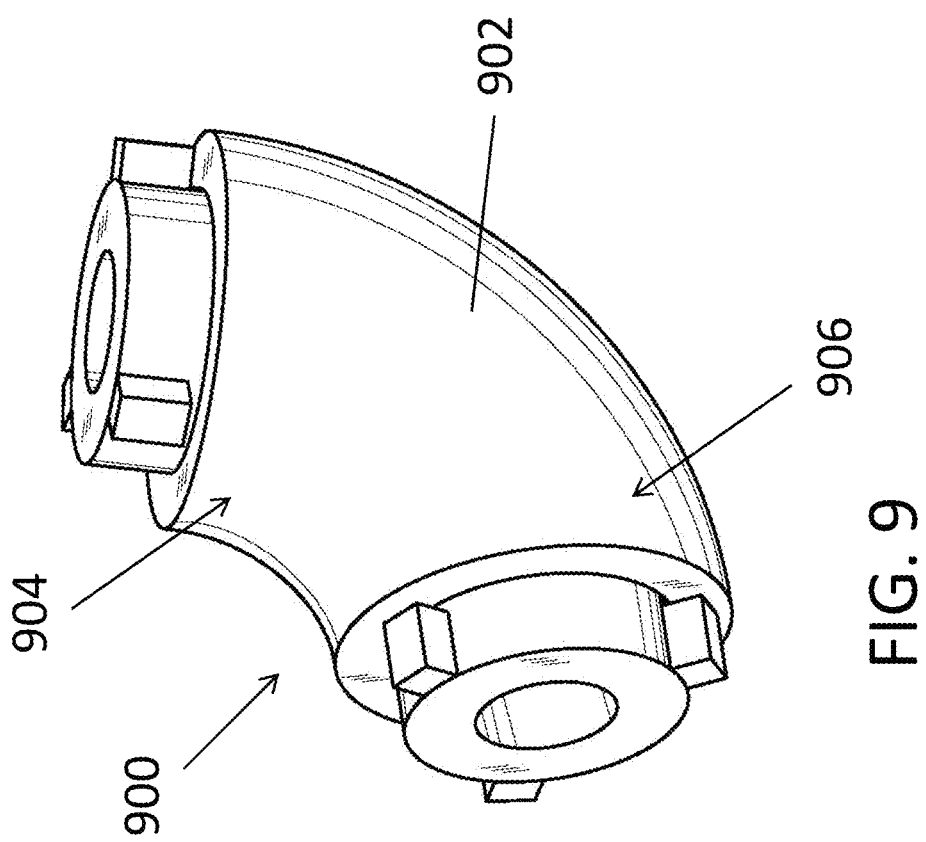
FIG. 9 is a perspective view of another exemplary intermediate universal connector, having an angular shape, in accordance with the present invention.
Figure 10:
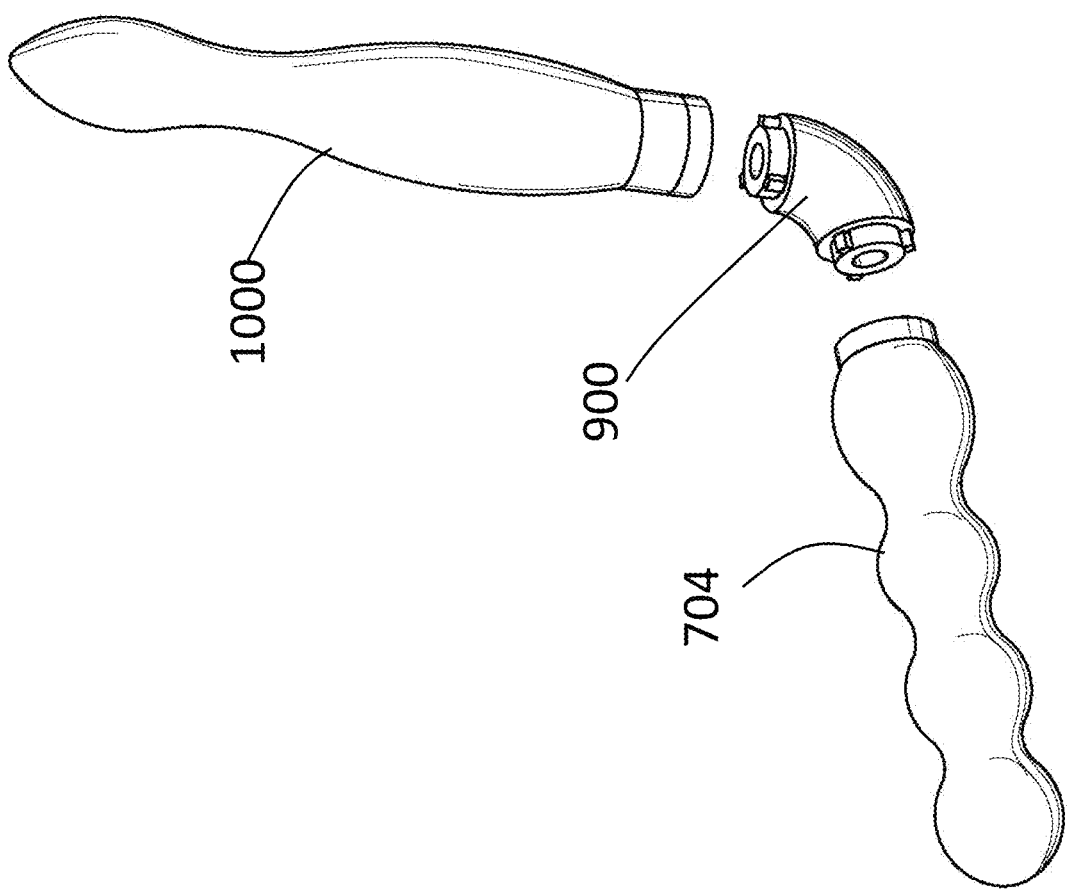
FIG. 10 is a perspective view of yet another exemplary embodiment of an interchangeable intimate accessory system with the angular intermediate universal connector of FIG. 9, shown unconnected, in accordance with the present invention.
Figure 11:
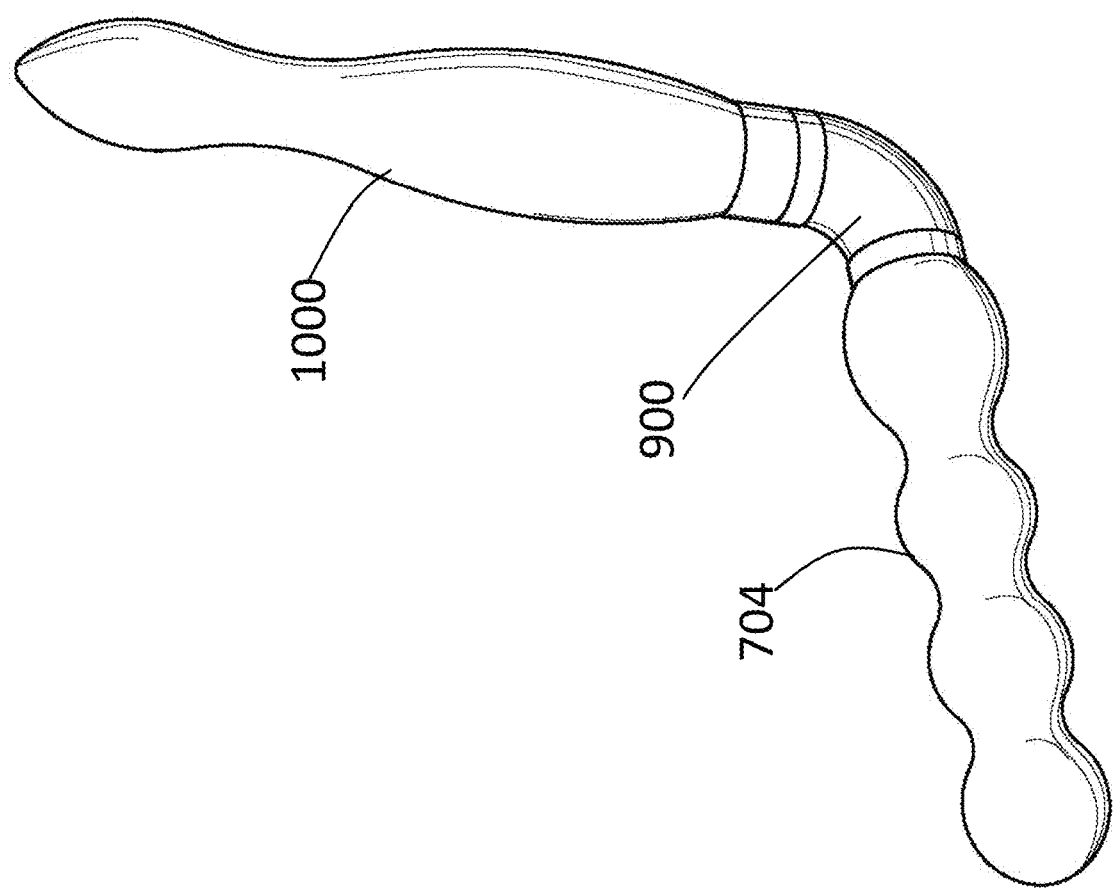
FIG. 11 is a perspective view of the interchangeable intimate accessory system of FIG. 12 with the angular intermediate universal connector of FIG. 9, shown connected together, in accordance with the present invention.

Referring now briefly to FIGS. 9-11, an alternative embodiment of an intermediate universal connector 900 is illustrated. The intermediate universal connector 900 includes a main body 902 that is formed as an angular-shaped body. In a further embodiment, the main body 902 may include a first arm portion 904 and a second arm portion 906. The first arm portion 904 and the second arm portion 906 may be disposed such that when the phallic devices are coupled to each arm portion 904, 906, the distal ends of the phallic devices are oriented at between 45 and 135 degrees relative to one another. In another embodiment, the distal ends of the phallic devices may be oriented at 360 degrees relative to one another. In other words, the first arm portion 904 and the second arm portion 906 may be disposed such that when the phallic devices are coupled to each arm portion 904, 906 the entire dual-ended device is formed as a U-shape. In such an embodiment, the intermediate universal connector 900 may itself be U-shaped. In other embodiments, the arm portions 904, 906 may be oriented at other angles relative to one another. In yet other embodiments, the intermediate universal connector 900 is flexible such that the degree of curvature is selectively adjustable by the user. Stated another way, each of the arm portions 904 and 906 may be moveable relative to one another so as to selectively change the orientation of the arms portions 904 and 906 relative to one another and thereby provide users with additional variety of use. In a further embodiment, the flexible intermediate universal connector 900 may be made of a flexible polymer-based material. In yet other embodiments, the intermediate universal connector 900 may also be provided in other shapes, such as a "T" shape for connection to three phallic devices in one configuration. Advantageously, providing intermediate universal connectors 900 in varying shapes provides varying configurations of the system 100 when the phallic devices are coupled thereto. As can be seen in FIGS. 10 and 11, the phallic devices 704 and 1000 coupled to the angular-shaped intermediate universal connector 900 provides the penetration ends (i.e., the distal ends) at a different orientation relative to one another, as compared to the intermediate universal connector 302. Accordingly, both the intermediate universal connector 900, 302, the phallic devices 102, 104, 704, 1000, and the end cover base portion 700 can be selectively interchangeable within the intimate accessory system 100 for variety and personalization.

Figure 17:
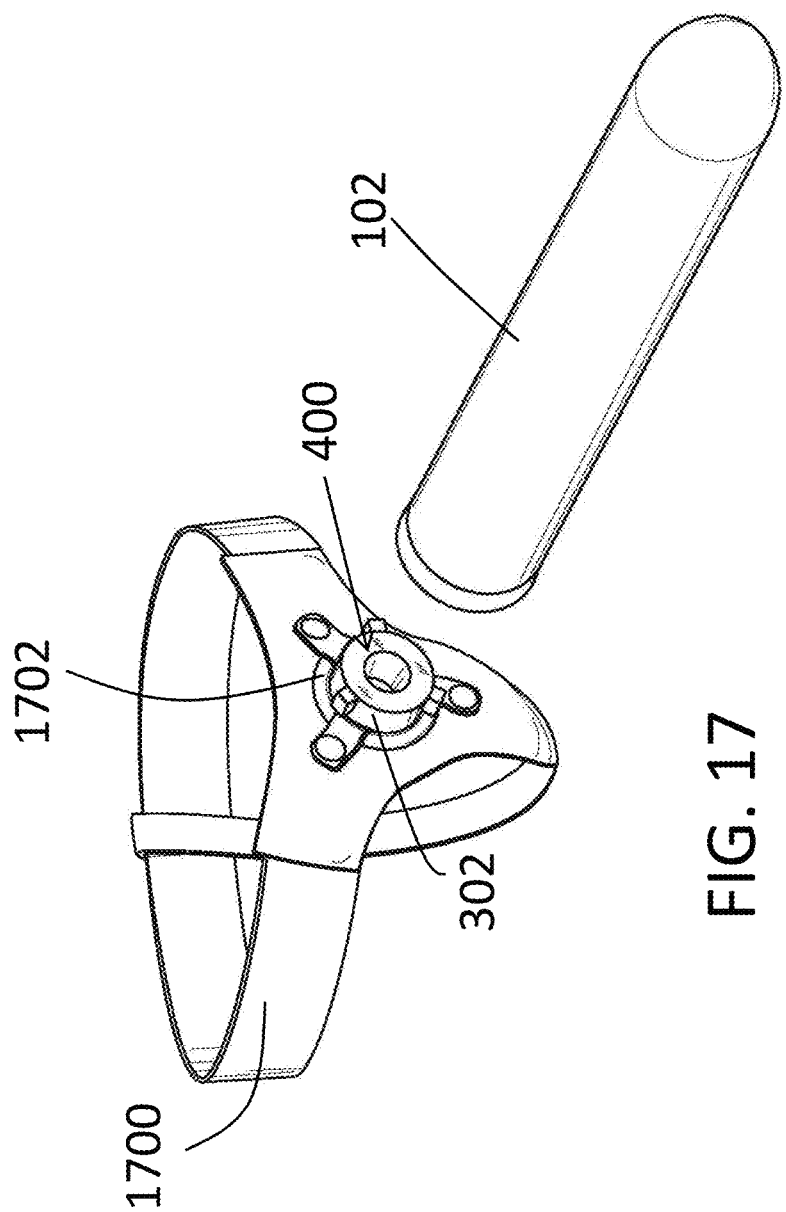
FIG. 17 is perspective view of a harness system in accordance with an embodiment of the present invention.
Figure 18:
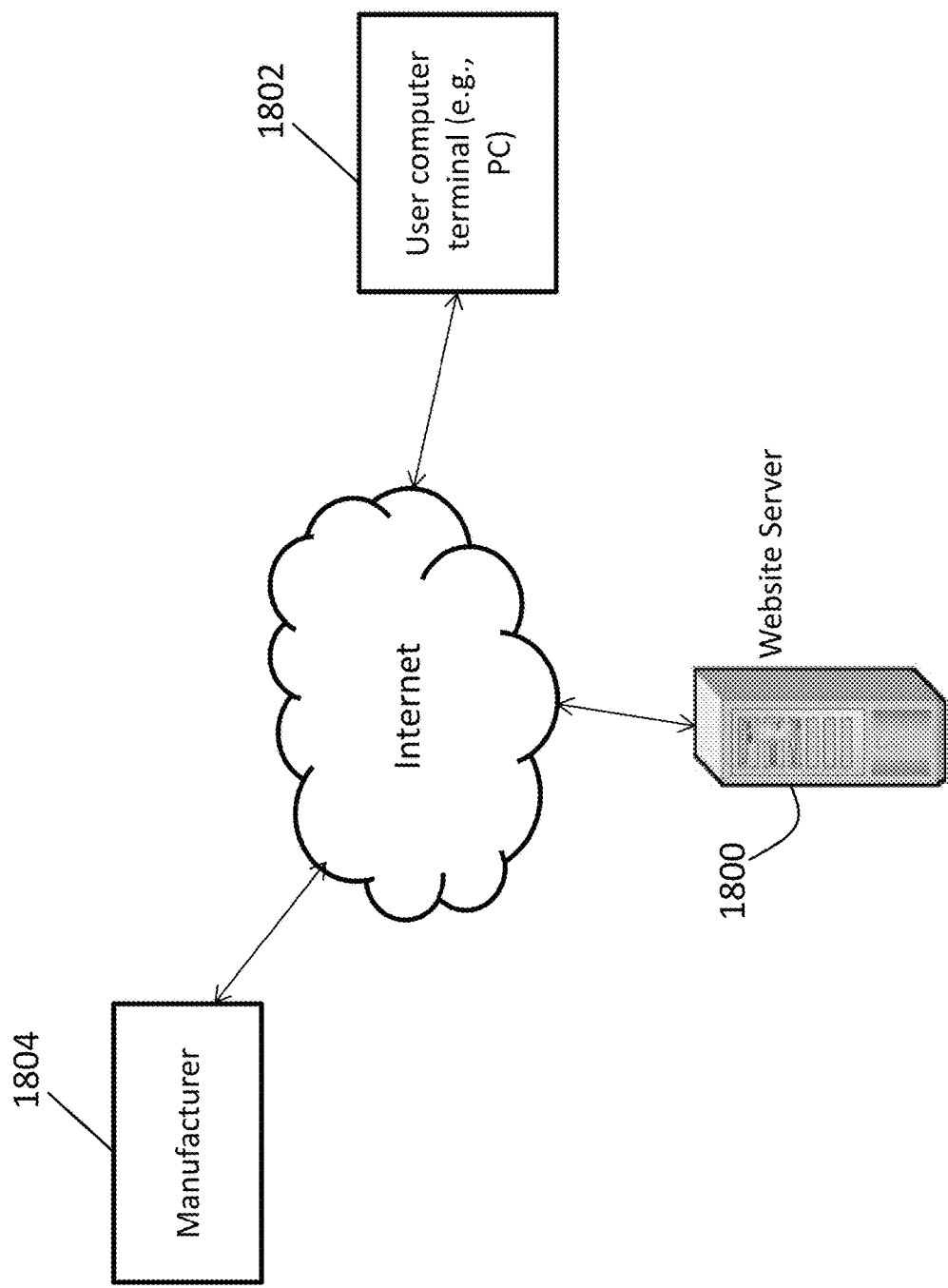
FIG. 18 is a schematic diagram of a network architecture in accordance with an embodiment of the present invention.

Referring now briefly to FIG. 17, an alternative configuration of the system 100 is illustrated for use with a harness 1700 having an o-ring 1702 disposed thereon. In the exemplary embodiment, the intermediate universal connector 302 may be couplable with the o-ring 1702. Further, the first end 400 of the intermediate universal connector 302 may be couplable with a mating connector on the phallic device 102 so as to secure the phallic devices to the harness 1700. In yet a further embodiment, the second end 402 of the intermediate universal connector 302 may be couplable with the end cover base portion 700 (not shown) on an interior area of the harness 1700 for added stability and hold. As is known in the art, the harness 1700 is operably configured to be worn on a portion of the human body, such as, for example a panty harness, as depicted in FIG. 17, or a facial harness.

Figure 12:
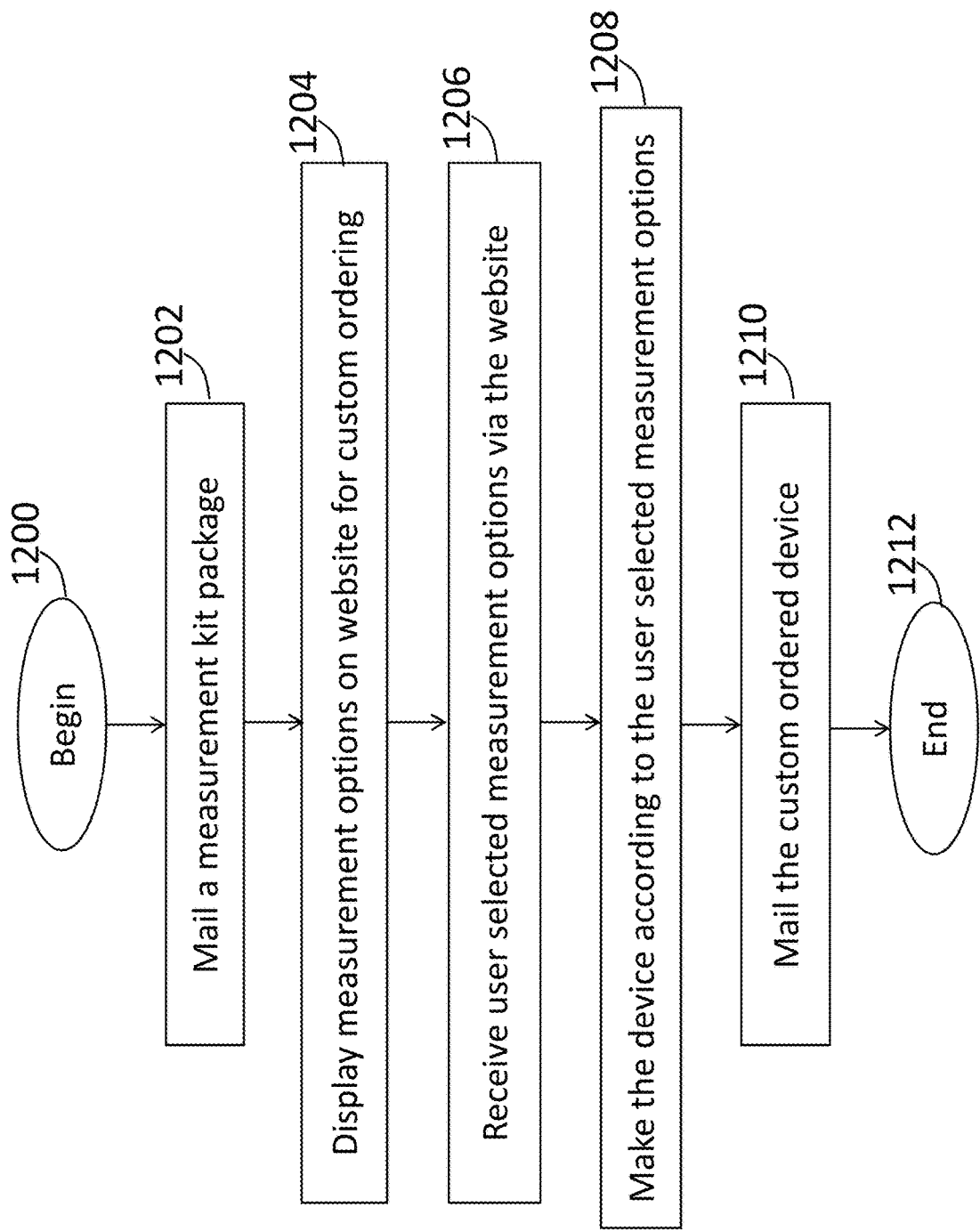
FIG. 12 is a block diagram of an exemplary process flow chart for custom ordering at least a portion of an interchangeable intimate accessory system in accordance with the present invention.
Figure 13:
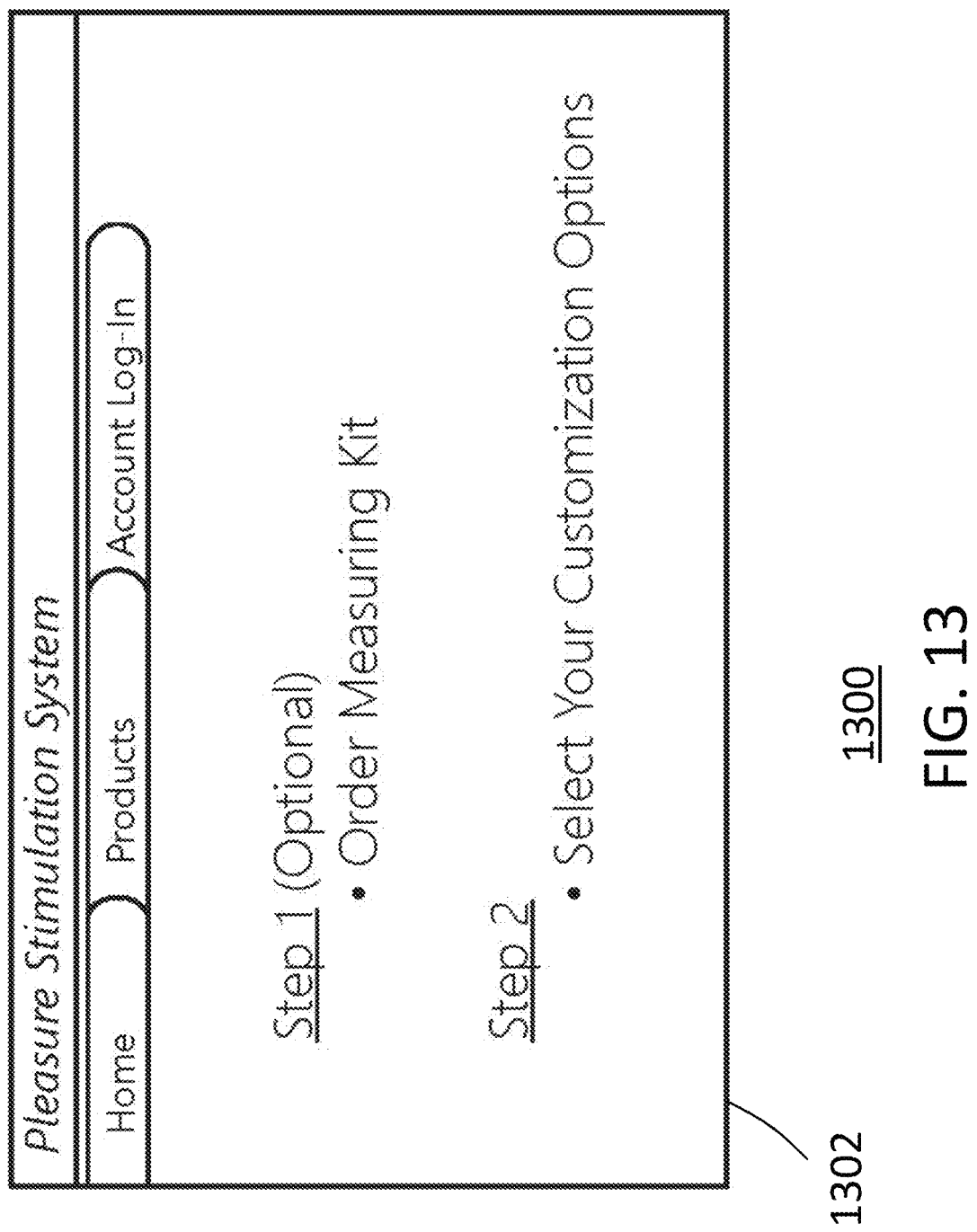
FIG. 13 is a schematic diagram of an exemplary website home page for custom ordering in accordance with the present invention.
Figure 14:
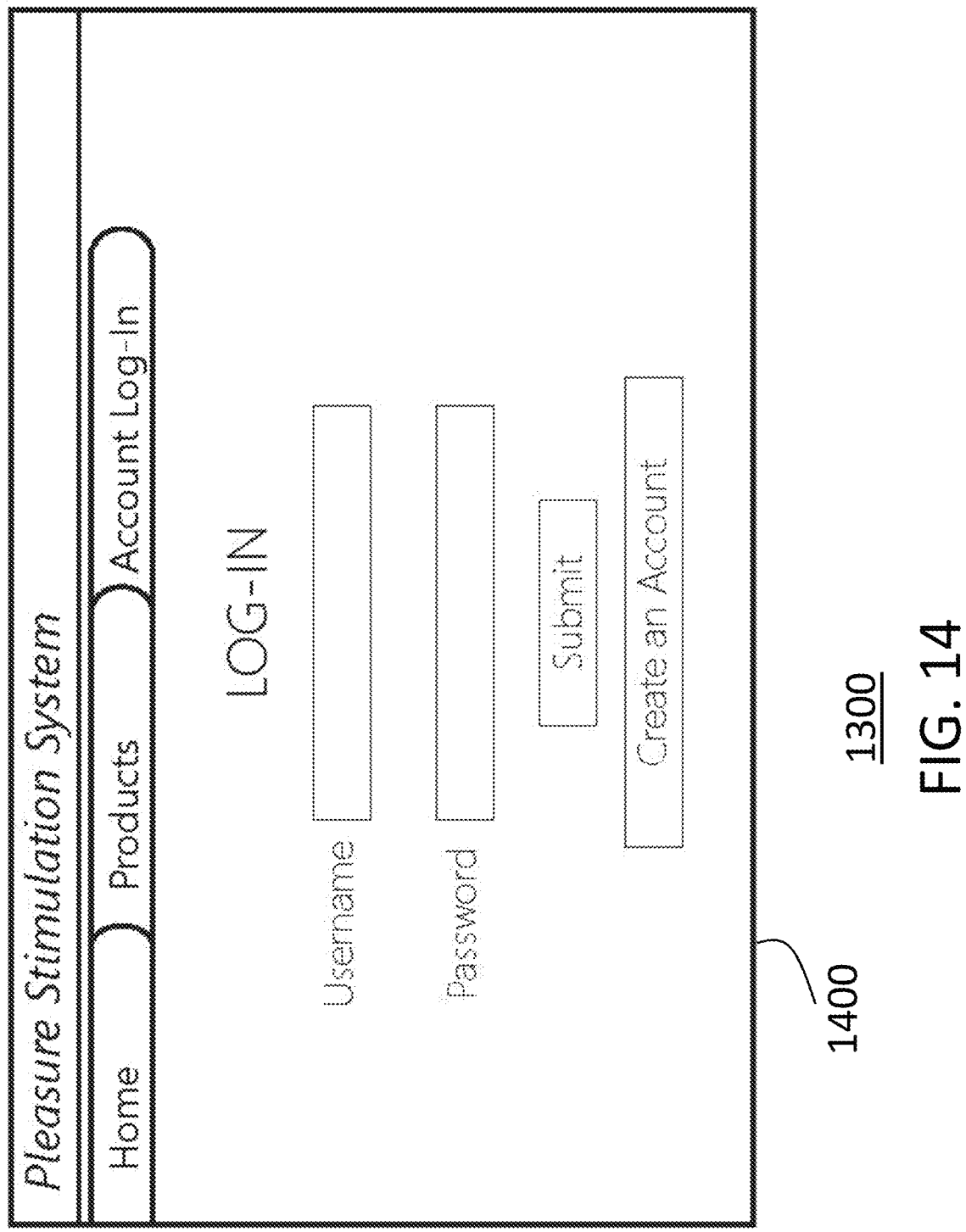
FIG. 14 is a schematic diagram of a login page for the website of FIG. 13 in accordance with the present invention.
Figure 15:
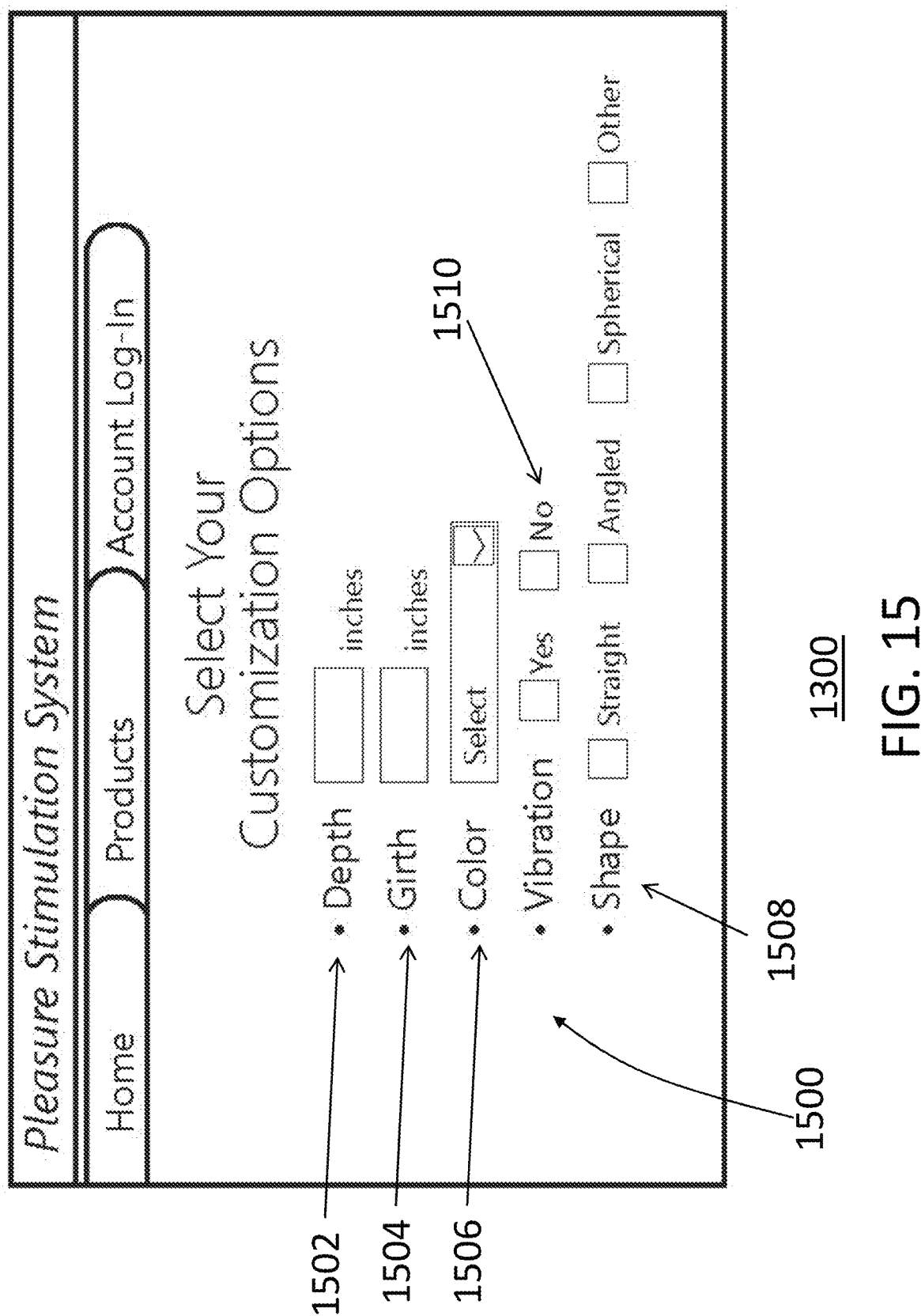
FIG. 15 is a schematic diagram of a webpage associated with the website of FIG. 13 for user-selection of personalized measurement options.

Referring now primarily to the flow chart of FIG. 12 and to the website screenshots in FIGS. 13-15, with brief reference to FIGS. 2-11 and 18, an exemplary method of ordering a personalized interchangeable intimate accessory system 100 is described.

Although FIG. 12 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 12 for the sake of brevity. In some embodiments, some or all of the process steps included in FIG. 12 can be combined into a single process.

The process may begin at step 1200 and may immediately proceed to step 1202, where a user may order a measurement kit 1600 (FIG. 16) to be physically mailed to the user, such as, for example, by Fedex, or the U.S. Postal Office. The measurement kit 1600 may be mailed to the user in an enclosed package. The measurement kit 1600 can be considered a phallic measurement kit 1600.

In one embodiment, there may be at least one website server 1800 having at least one processor and operably configured to provide an Internet website 1300 for custom-ordering phallic devices, such as the interchangeable phallic devices discussed herein above. The Internet website 1300 may display, on a computer display of a user computer terminal (e.g., personal computer or mobile device) 1802, accessing the website 1300, a home page 1302. The home page 1302 may display options allowing the user to 1) pre-order the measurement kit 1600 to assist the user with determining a preferred set of phallic dimensions, and/or 2) selecting the phallic dimensions and other customization options. Users that already know their preferred set of phallic dimensions may omit the measurement kit 1600. Other users may desire to receive the novel and inventive measurement kit 1600 before selecting the phallic dimensions via the website 1300.

In one embodiment, the user may be required to login to a login page 1400. As is generally known in the website arts, the login page 1400 may require the user to enter a unique username and password combination in order to log in to the user's account. If the user has not yet created an account, the user may be required to create an account, by clicking on a "create an account" button or icon. Advantageously, by providing a user account the user's preferences and previous orders may be saved on the server 1800 and associated with the unique user each time he or she logs in.

In step 1204, the server 1800 may display a first display portion 1500 of the website 1300 at the user computer terminal 1302. The first display portion 1500 may display a plurality of user selection options for at least one phallic device (e.g., 102, 104, 704, 1000). The plurality of user selection options should include at least two user selection options for a phallic depth measurement 1502 and at least two user selection options for a phallic girth measurement 1504. In other words, the first display portion 1500 should allow the user to input/select at least two options for the phallic depth measurement 1502 and should allow the user to input/select at least two options for the phallic girth measurement 1504. Stated another way, the user selection options for the personalized phallic device and/or system 100 should be configured to be selectable by the user, from among a plurality of options, through the first display portion 1500 of the website 1300. In a further embodiment, the first display portion 1500 may provide this, for example, with a drop down list of measurement options, or a user input field that allows the user to manually enter measurement options corresponding to measurement options provided by the phallic measurement kit 1600. In yet other embodiments, other website user-input website elements may be used to allow the user to select from various options.

In other embodiments, the first display portion 1500 may provide other options in addition to phallic depth and girth measurements 1502 and 1504, such as, for example, a color option 1506 and a shape option 1508 of one or more of the phallic devices to be ordered alone or to be combined in the system 100. The color option 1506 may include any known colors. The shape option 1508 may include any known shape of such phallic devices, as discussed herein above, such as, for example, straight, angled spherical, etc. In another embodiment, there may be provided at the website 1300 a vibration option 1510 that may allow users to select whether they want one or more of the phallic devices to vibrate.

In a further embodiment, the first display portion 1500 or a second web page associated with the website 1300 may allow the user to select measurements 1502 and 1504 and other options for a second phallic device. In yet further embodiments, the first display portion 1500 or another web page associated with the website 1300 may allow the user to select from one of a plurality of intermediate universal connectors, such as, for example, the intermediate universal connectors 302 and 900, described herein above. In yet a further embodiment, the first display portion 1500 or another web page associated with the website 1300 may allow the user to optionally select the end cover base portion 700. Accordingly, the various features associated with the interchangeable intimate accessory system 100 of the present invention can be selected and personalized for the user through selectable options provided on the website 1300. In other embodiments, the user may use the website 1300 to order personalized phallic devices alone, i.e. not combined in the system 100.

Importantly to embodiments of the present invention, the measurement input/selection options available at the website 1300 should correspond to the measurements indicated on measurement tools provided within the phallic measurement kit 1600. In one embodiment, the phallic measurement kit 1600 may include at least one phallic depth measurement tool 1602 and at least one phallic girth measurement tool 1604.

In a preferred embodiment, the phallic depth measurement tool 1602 provides at least a dual-sensory indication of the plurality of user-selectable phallic depth measurements 1502. The phallic depth measurement tool 1602 may include a visual indication 1606 visually identifying for the user each of the plurality of user-selectable phallic depth measurements, such as, for example, a plurality of gradient markings 1606 visible on and extending along a length of an exterior surface of the tool 1602.

In a further embodiment, the phallic depth measurement tool 1602 also includes a tactile indication for the user to identify a preferred one of the plurality of user-selectable phallic depth measurements 1502. More specifically, the phallic depth measurement tool 1602 may be configured to provide a tactile indication for an interior surface of the user's orifice (e.g., vagina walls). In one such embodiment, the phallic depth measurement tool 1602 may be formed as an elongated tubular body disposed for insertion within the user's orifice. In a further embodiment, the phallic depth measurement tool 1602 may be considered a universal hollow tubular vagina inserter with each of the plurality of gradient markings 1606 visually indicating the plurality of user-selectable phallic depth measurements 1502 provided via the Internet website 1300. For example, in an embodiment where the Internet website 1300 provides, for example, ten different user-selectable phallic depth measurements 1502, there should also be provided ten gradient markings 1606 on the phallic depth measurement tool 1602 that correspond to the user-selectable phallic depth measurements 1502 provided via the website 1300. Advantageously, by providing dual-sensory indication tools 1602 and 1604 in the phallic measurement kit 1600 the user may be able to more accurately determine a desired measurement through both senses, without actually having to purchase the phallic device to try it out.

Figure 16:
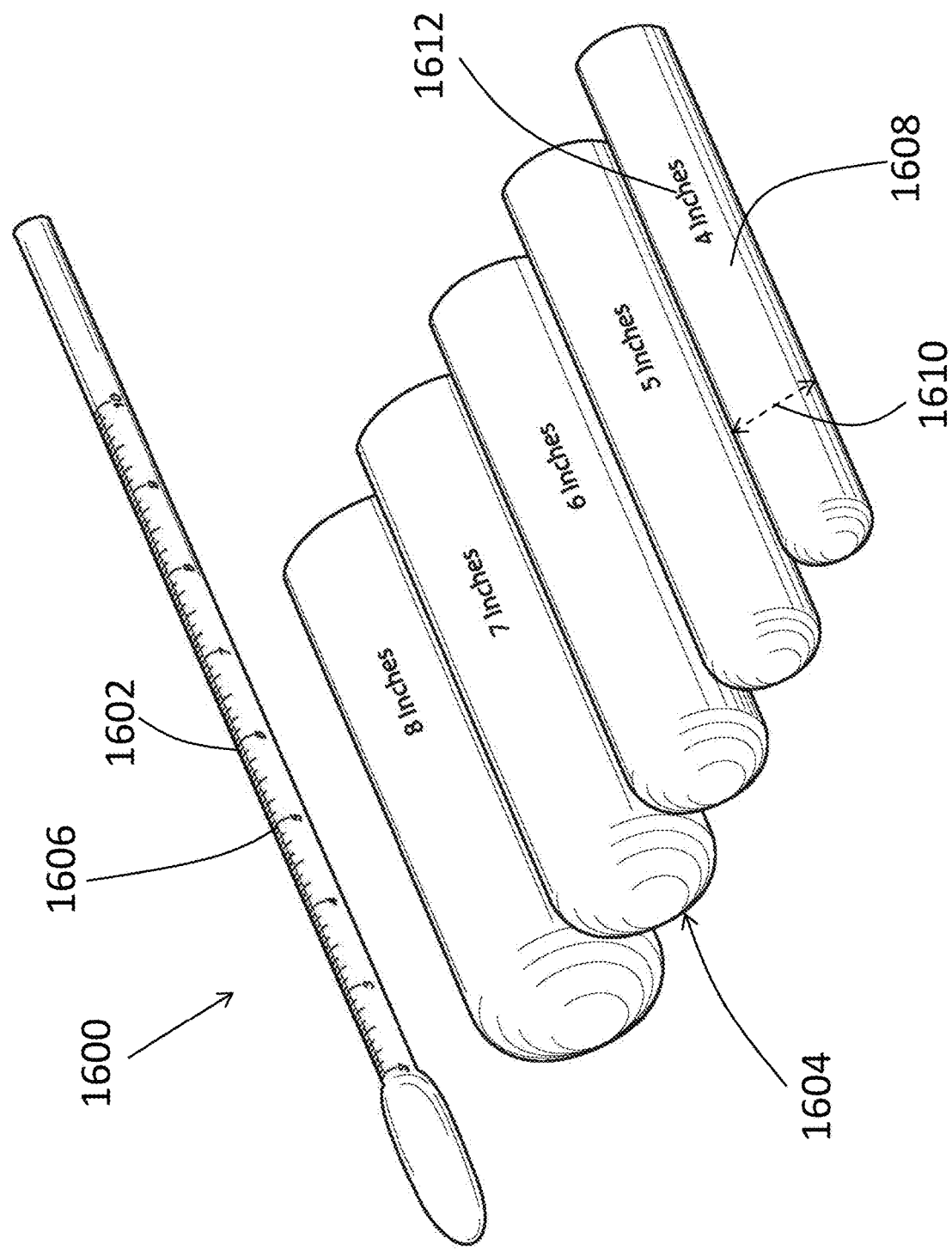
FIG. 16 is a perspective view of a phallic measurement kit in accordance with an embodiment of the present invention.

In a preferred embodiment, the phallic girth measurement tool 1604 provides at least a dual-sensory indication of a plurality of user-selectable phallic girth measurements 1504. The phallic girth measurement tool 1604 may include a visual indication visually identifying for the user each of the plurality of user-selectable phallic girth measurements 1504, such as, for example, a plurality of tubular bodies 1608 each having a different visually identifiable diameter 1610 and disposed for insertion within and tactile contact with the interior surface of the user's orifice (e.g., vagina). The visually identifiable diameter may be formed as a marking 1612 visible on an exterior surface of each of the tubular bodies 1608 indicating to the user a specific user-selectable girth measurement 1504 diameter, as shown in FIG. 16.

In a further embodiment, the phallic girth measurement tool 1604 also includes a tactile indication for the user to identify a preferred one of the plurality of user-selectable phallic girth measurements 1504. More specifically, the phallic girth measurement tool 1604 may be configured to provide a tactile indication for the interior surface of the user's orifice (e.g., vagina walls). In one such embodiment, the phallic girth measurement tool 1604 includes the plurality of tubular bodies 1608, each tubular body 1608 disposed for insertion within the user's orifice and having a different girth dimension. In other words, each tubular body 1608 may have a diameter 1610 that is different than a diameter 1610 of each of the other tubular bodies 1608, with each diameter 1610 corresponding to one of the plurality of user-selectable phallic girth measurements 1504 provided via the website 1300. In another embodiment, the bodies 1608 may be more circular than tubular. In yet other embodiments, the bodies 1608 may include a string, or other elongated, externally graspable portion, such as, a tab, that allows the user to more easily extract the body 1608 from the user's orifice after insertion. In one embodiment, the number of bodies 1608 provided in the measurement kit 1600 may correspond to the number of user-selectable phallic girth measurement options 1504 available via the website 1300. For example, in an embodiment where the website 1300 provides five different girth measurements 1504, the measurement kit 1600 may include five bodies 1608 each having a different diameter corresponding to the user-selectable girth measurements 1504 provided via the website 1300.

In step 1206, the user may input the selected measurements via the website 1300 and the server 1800 may then receive the user selected measurement options. In one embodiment, the user may, for example, select a "submit" or "order" button that may indicate that the user desires to submit the order to be made according to the user's input. In other words, the server 1800 may receive, from the user computer terminal 1802, a request to make the one or more phallic devices and/or the system 100 according to the user selections, input via the website 1300, for the phallic depth and girth measurements, as discussed herein above. As a result of the request, in step 1208, the phallic devices and/or the system 100 may be made according to the user's selections input via the website 1300. The phallic devices and/or the system 100 may be submitted to a manufacturer 1804. The manufacturer 1804 may make the phallic devices and/or the system 100 by three-dimensional printing or other more traditional manufacturing techniques, such as, for example, a three-dimensional mold. In step 1210, after being made according to the user's selections, the personalized phallic devices and/or the system 100 may be mailed to the user at a physical address indicated by the user, for example, in his/her website account. The process may end at step 1212.

A novel and efficient interchangeable intimate accessory system has been disclosed. Embodiments of the invention provide for a system with at least a first phallic device and a second phallic device removably couplable with one another for selective dual or individual use. In addition, embodiments of the invention provide for an intermediate universal connector between first and second phallic devices for removably coupling the phallic devices to one another. Additional embodiments of the present invention provide for an end cover base portion that fits over a connector end of the phallic device to cover the connector end and also provide a gripping surface for individual use of the phallic device, when not being used in a dual configuration. Furthermore, some embodiments of the present invention provide for a novel and inventive phallic measurement kit that provides users with at least a dual-sensory indication of selectable girth and depth measurement options. Yet further embodiments of the present invention include a website configured to receive measurement options indicated in the measurement kit for ordering and personalizing the phallic devices according the users' personal desires and preferences.

What is claimed is:

1. A system comprising:
   at least one server operably configured to provide an Internet website for custom-ordering phallic devices and to cause at least one processor to:
   display a first display portion of the Internet website, at a user computer terminal, including a plurality of user selection options for at least one custom-order phallic device with at least two user selection options for a phallic depth measurement and at least two user selection options for a phallic girth measurement, the plurality of user selection options for the at least one custom-order phallic device are configured to be selected by a user through the first display portion of the Internet website; and
   a phallic measurement kit including:
   at least one phallic depth measurement tool providing at least a dual-sensory indication of a plurality of user-selectable phallic depth measurements corresponding to the at least two user selection options for the phallic depth measurement provided via the first display portion of the Internet website; and
   at least one phallic girth measurement tool providing at least a dual-sensory indication of a plurality of user-selectable phallic girth measurements corresponding to the at least two user selection options for the phallic girth measurement provided via the first display portion of the Internet website.

2. The system in accordance with claim 1, wherein the at least one server is further operably configured to cause the at least one processor to:
receive, from the user computer terminal, via a second display portion of the Internet website, a request to make the at least one custom-order phallic device according to at least the user selections, input via the Internet website, of the plurality of user selection options for the phallic depth measurement and the phallic girth measurement.

3. The system in accordance with claim 1, wherein:
the dual-sensory indication provided by the at least one phallic depth measurement tool includes a visual indication identifying each of the plurality of user-selectable phallic depth measurements and a tactile indication for an interior surface of the user's orifice corresponding to each of the plurality of user-selectable phallic depth measurements; and
the dual-sensory indication provided by the at least one phallic girth measurement tool includes a visual indication identifying each of the plurality of user-selectable phallic girth measurements and a tactile indication for an interior surface of the user's orifice corresponding to each of the plurality of user-selectable phallic girth measurements.

4. The system in accordance with claim 3, wherein:
the tactile indication for the at least one phallic depth measurement tool is formed as an elongated tubular body disposed for insertion within the user's orifice and the visual indication for the at least one phallic depth measurement tool includes a plurality of gradient markings visible on and extending along a length of the elongated tubular body.

5. The system in accordance with claim 4, wherein:
the visual indication and the tactile indication for the at least one phallic girth measurement tool includes a plurality of tubular bodies each having a different visually identifiable diameter and disposed for insertion within and tactile contact with an interior surface of the user's orifice.

6. The system in accordance with claim 1, wherein:
the at least one phallic depth measurement tool is formed as a universal hollow tubular vagina inserter with a plurality of gradient markings each visually indicating the plurality of user-selectable phallic depth measurements provided via the Internet website and the universal hollow tubular vagina inserter disposed for insertion within the user's orifice for a tactile indication of a desired one of the plurality of user-selectable phallic depth measurements; and
the phallic girth measurement tool including a plurality of tubular bodies disposed for vaginal insertion, each tubular body having a diameter that is different than a diameter of each of the other tubular bodies and each diameter corresponding to one of the plurality of user-selectable phallic girth measurements provided via the Internet website.

7. The system in accordance with claim 1, wherein the at least one custom-order phallic device includes:
a first phallic device having a distal end and a proximal end, the distal end of the first phallic device being shaped and configured for sexual application to a human orifice and the proximal end of the first phallic device being formed as a first connector;
a second phallic device having a distal end and a proximal end, the distal end of the second phallic device being shaped and configured for sexual application to a human orifice and the proximal end of the second phallic device being formed as a second connector, the first phallic device and the second phallic device being removably couplable to one another, via coupling of the first and second connectors, so as to provide a dual-ended configuration when coupled together and an individual-use configuration when not coupled together; and
at least one of the first phallic device and the second phallic device is ordered via the Internet website to be made according to one of the plurality of user-selectable phallic depth measurements and one of the plurality of user-selectable phallic girth measurements identified via the phallic measurement kit and selected, at the user computer terminal, via the Internet website.

8. The system in accordance with claim 1, wherein the plurality of user selection options for the at least one custom-order phallic device included in the first display portion of the Internet website further includes:
a color option;
a vibration option; and
a plurality of phallic device shape options.

9. A method of making at least one personalized phallic device, the method comprising:
mailing, to a user, an enclosed package including a phallic measurement kit with:
at least one phallic depth measurement tool providing at least a dual-sensory indication of a plurality of user-selectable phallic depth measurements corresponding to at least two user selection options for the user-selectable phallic depth measurements provided via a first display portion of an Internet website; and
at least one phallic girth measurement tool providing at least a dual-sensory indication of a plurality of user-selectable phallic girth measurements corresponding to at least two user selection options for the user-selectable phallic girth measurements provided via the first display portion of the Internet website;
after mailing to the user, displaying, by at least one server, the first display portion of the Internet website, at a computer terminal associated with the user, the first display portion displaying a plurality of user selection options for at least one custom-order phallic device including the at least two user selection options for the user-selectable phallic depth measurement and the at least two user selection options for the user-selectable phallic girth measurements, the plurality of user selection options for the at least one custom-order phallic device are configured to be selected by the user through the first display portion of the Internet website;
receiving, by the at least one server, from the computer terminal associated with the user, a request to make the at least one custom-order phallic device according to at least the user selections, input via the Internet website, corresponding to the plurality of user selection options for the phallic depth measurement and the phallic girth measurement; and
as a result of receiving the request, causing the at least one custom-order phallic device to be made by one of three-dimensional printing and manufacturing with a three-dimensional mold according to at least the user selections, input via the Internet website, corresponding to the plurality of user selection options for the phallic depth measurement and the phallic girth measurement.

* * * * *